(12) United States Patent
Hwang

(10) Patent No.: US 10,821,226 B2
(45) Date of Patent: *Nov. 3, 2020

(54) INFUSION SET WITH SAFETY DEVICE

(71) Applicant: Becton, Dickinson and Company, Franklin Lakes, NJ (US)

(72) Inventor: Charles Hwang, Wellesley, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 96 days.

This patent is subject to a terminal disclaimer.

(21) Appl. No.: 15/708,710

(22) Filed: Sep. 19, 2017

(65) Prior Publication Data

US 2018/0001020 A1 Jan. 4, 2018

Related U.S. Application Data

(62) Division of application No. 13/646,582, filed on Oct. 5, 2012, now Pat. No. 9,789,250.

(51) Int. Cl.
| *A61M 5/162* | (2006.01) |
| *A61M 5/158* | (2006.01) |
| *A61M 39/08* | (2006.01) |
| *A61M 39/20* | (2006.01) |
| *A61M 5/32* | (2006.01) |
| *A61M 39/10* | (2006.01) |

(52) U.S. Cl.
CPC .......... *A61M 5/1626* (2013.01); *A61M 5/158* (2013.01); *A61M 5/3202* (2013.01); *A61M 39/08* (2013.01); *A61M 39/20* (2013.01); *A61M 2039/1066* (2013.01)

(58) Field of Classification Search
CPC .......... A61M 2005/1585; A61M 5/162; A61M 5/1626; A61M 5/3202
See application file for complete search history.

(56) References Cited

U.S. PATENT DOCUMENTS

| 3,670,727 A | 6/1972 | Reiterman |
| 5,322,515 A * | 6/1994 | Karas .................... A61M 39/04 128/919 |
| 5,545,143 A | 8/1996 | Fischell |
| 6,017,328 A | 1/2000 | Fischell et al. |

(Continued)

FOREIGN PATENT DOCUMENTS

| FR | 1209337 | 3/1960 |
| JP | 52-080585 U | 12/1975 |

(Continued)

OTHER PUBLICATIONS

Intrafix® Primeline, B. Braun, Sharing Expertise, Meet All Your Routine Fluid Administration Needs With State-of-the-Art Technolgy and Great Value, 3 pages; downloaded from Internet on Aug. 8, 2012.

(Continued)

*Primary Examiner* — Matthew F Desanto
(74) *Attorney, Agent, or Firm* — Dickinson Wright PLLC

(57) ABSTRACT

An infusion base for attachment to a user of an infusion set comprises an adapter having a lower portion, an inner wall portion, and a gap between the lower portion and the inner wall portion. At least one of the lower portion and the inner wall portion is configured to receive an attachment.

17 Claims, 16 Drawing Sheets

(56) References Cited

U.S. PATENT DOCUMENTS

| | | | |
|---|---|---|---|
| 6,106,502 A * | 8/2000 | Richmond | A61J 1/10 604/246 |
| 7,297,138 B2 | 11/2007 | Fangrow, Jr. | |
| 7,314,463 B2 | 1/2008 | Fangrow, Jr. | |
| 7,331,939 B2 | 2/2008 | Fangrow, Jr. | |
| 7,407,491 B2 | 8/2008 | Fangrow, Jr. | |
| 7,494,481 B2 | 2/2009 | Moberg et al. | |
| 7,520,867 B2 | 4/2009 | Bowman et al. | |
| 7,892,216 B2 | 2/2011 | Fangrow, Jr. | |
| 7,935,090 B2 | 5/2011 | Patton | |
| 9,789,250 B2 * | 10/2017 | Hwang | A61M 5/1626 |
| 2007/0185441 A1 * | 8/2007 | Fangrow, Jr. | A61M 5/158 604/93.01 |
| 2008/0243085 A1 | 10/2008 | DeStefano | |
| 2009/0163878 A1 | 6/2009 | Moberg et al. | |

FOREIGN PATENT DOCUMENTS

| | | |
|---|---|---|
| JP | 2000-342686 A | 12/2000 |
| JP | 2003-024455 A | 1/2003 |
| JP | 2005-518907 A | 6/2005 |
| JP | 2007-511325 A | 5/2007 |
| JP | 2012-115673 A | 6/2012 |

OTHER PUBLICATIONS

Intrafix® Primeline Classic, B. Braun, Sharing Expertise, The Standard IV Set, 4 pages; downloaded from Internet on Aug. 8, 2012.

Luer Taper, http://en.wikipedia.org.wiki/Luer_taper, 2 pages; downloaded from Internet on Jul. 24, 2012.

ISO 594-1, ISO 594-2 & Other Luer Fitting Tests, http://www.testedandproven.com/product-testing/luer-fiffing-testing, 4 pages; downloaded from Internet on Aug. 15, 2012.

European Search Report dated Nov. 27, 2013 issued by the European Patent Office in counterpart European Application No. 13187145.1.

* cited by examiner

INFUSION SET WITH SAFETY DEVICE

This application is a division of U.S. Nonprovisional application Ser. No. 13/646,582, filed Oct. 5, 2012, the entire disclosure of which is hereby incorporated by reference.

FIELD OF THE INVENTION

The present invention relates generally to infusion sets that use a rigid infusion cannula or introducer having a sharp or piercing end that penetrates the skin of a patient. More particularly, the present invention relates to protecting the rigid infusion cannula or introducer attached to an infusion set before the cannula pierces the skin of a user, and/or after the rigid infusion cannula or introducer has been removed from the patient.

BACKGROUND OF THE INVENTION

Diabetes patients use some form of daily insulin therapy to maintain close control of their glucose levels. Infusion pump therapy is one preferred method. Infusion pump therapy occurs via an infusion cannula (i.e., an infusion needle or a flexible catheter) and requires an infusion pump. Infusion pump therapy offers the advantages of continuous infusion of insulin, precision dosing, and programmable delivery schedules.

The use of an infusion pump requires the use of a disposable component, typically referred to as an infusion set, tubing set, which administers insulin from a reservoir that is pumped into the skin of the user. An infusion set typically consists of a pump connector, a length of tubing, and a hub or base from which an infusion cannula extends. The base has an adhesive that attaches the base on the skin surface during use. The base, with the infusion cannula attached thereon, may be applied to the skin manually or with the aid of a manual or automatic insertion device.

There are many available types of infusion sets incorporating various types of infusion cannulas, including steel needle infusion sets and soft catheter sets. Soft catheter sets can be inserted into a patient with the aid of a steel introducer needle, which is later removed from the patient, leaving the soft catheter in place. The steel cannula infusion set utilizes a steel needle or cannula that is secured to the base.

An advantage of the steel cannula infusion sets is that the steel cannulas, due to their rigidity are less susceptible to kinking. Kinking occurs when the infusion cannula, be it rigid or soft, is unable to resist mechanical forces that may bend or twist the infusion cannula, resulting in a restricted flow of infusate exiting the catheter. Another advantage of a steel cannula infusion set is that the steel cannula pierces the patient's skin without the need for a separate introducer needle, as in soft catheter sets.

A steel cannula typically is protected by a disposable protective tube (typically made of plastic) that is attached to the base, surrounding the steel cannula, prior to use, and such attachment generally is not very secure. The user removes the disposable tube before the steel cannula is inserted into the user's skin. The protective tube is generally disposed of.

A steel cannula infusion set is illustrated in FIGS. 1-5
FIG. 1 illustrates a steel cannula infusion set 1 having a plastic fluid connector or hub 22 that is detachably attached to a plastic base 10, a fluid tubing set 28, and a plastic connector 26 which is attachable to a pump (not shown). The connector 26 includes an outer wall 262. The line set 20 includes the hub 22 and the fluid tubing set 28. The line set 20 is attached to or detached from the base 10, as illustrated in FIGS. 2 and 3.

FIG. 2 is a top view of the infusion set 1, illustrated with the hub 22 attached to the base 10. An adhesive pad 19 is attached to the base 10 and is configured to be attachable to the skin of the user. FIG. 3 illustrates a view of the infusion set 1, wherein the line set 20 is detached from the base 10. The base 10 includes an infusion adapter 14, to which the steel cannula 13 is attached.

FIG. 4 is a cross-sectional view of the infusion set 1, taken along lines 4-4 of FIG. 1, that more clearly illustrates how the infusate (insulin) is pumped into the steel cannula 13. The hub 22 of the line set 20 includes a hub port 25 that receives the fluid tubing set 28. The hub 22 includes a flow cannula 24. The base 10 includes a main base portion 12 and the adapter 14 includes a cylindrical lower portion 16, to which is attached the steel cannula 13, and a cylindrical inner wall portion 17 that is spaced apart from the lower portion 16. A pre-slit septum 18 encloses an upper portion of the adapter 14, when the hub 22 is not attached to the infusion base 10, as illustrated in FIGS. 3 and 5.

When the hub 22 is attached to the base 10, the flow cannula 24 penetrates the pre-slit septum 18 of the base 10 so that the steel cannula 13 is in fluid communication with the fluid tubing set 28, via channel 11. This allows the insulin from the pump (not shown) to flow from the fluid tubing set 28 into the steel cannula 13 and the insulin exits the distal opening or tip 131 of the steel cannula 13 into the patient.

FIG. 5 illustrates a cylindrical protector 30 attached to the base 10 to protect the steel cannula 13. Prior to use, the protector 30, which is form-fit in the base 10, is removed, and the protector 30, typically a tubular structure made of plastic, is disposed of.

A problem arises when a steel cannula infusion set is to be disposed. When the steel cannula 13 is removed from the user, which may be two or three days after initial insertion, the user may no longer have the disposable protector 30 or protective tube to cover the steel cannula 13 that may now contain bodily fluids. Even if the disposable protective tube 30 were available, since the attachment to the base 10 is not very secure, the protective tube 30 could easily be detached from base 10 to expose the used steel cannula 13.

A user is supposed to dispose of the steel cannula infusion set 1 in a sharps container designed for disposal of items that include a sharp needle, such as the infusion set 1 and syringes. However, a sharps container may not be readily available when a user wishes to dispose of and replace a used steel infusion set 1.

Accordingly, a need exists for an improved infusion set design and construction that can securely dispose of used steel needle infusion sets such that the steel cannula is not exposed, in order to protect people from such contact.

SUMMARY OF THE INVENTION

Objects of the present invention are to provide an infusion base to securely receive a protective element. In accordance with an aspect of the present invention, the protective element can be the connector of the fluid tubing set.

An objective of the present invention is to provide connecting elements, such as male threads and reciprocal female grooves, on the infusion base and the connector of the fluid tubing set for engagement and disengagement.

Another object of the present invention is to provide one or more flexible tabs on the infusion base that can receive the connector and resist its detachment therefrom.

These and other objects are substantially achieved by modifying elements of an infusion base to protect a steel cannula from unwanted contact.

BRIEF DESCRIPTION OF THE DRAWINGS

The various objects, advantages and novel features of the exemplary embodiments of the present invention will be more readily appreciated from the following detailed description when read in conjunction with the appended drawings, in which.

DETAILE DESCRIPTION OF THE EXEMPLARY EMBODIMENTS

Figure 6:
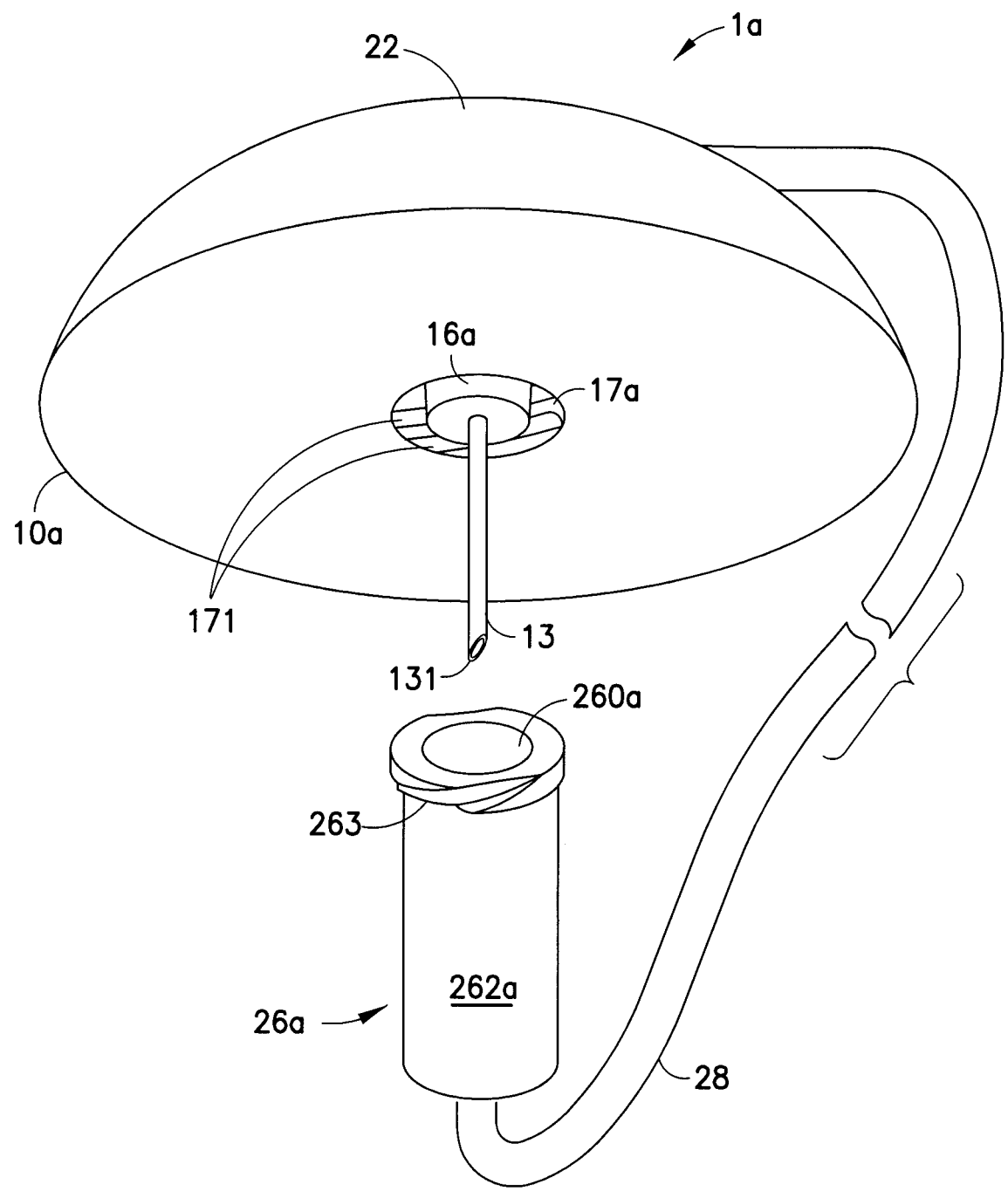
FIG. 6 is a perspective view of an exemplary infusion set of the present invention.
Figure 7:
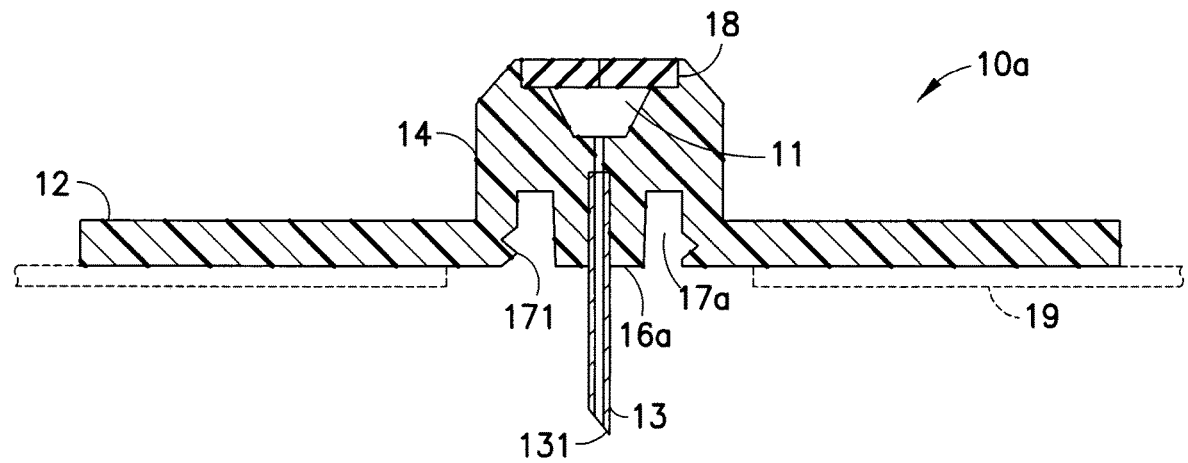
FIG. 7 is a cross-sectional view of the base of the infusion set of FIG. 6, after the hub has been removed from the base.
Figure 8:
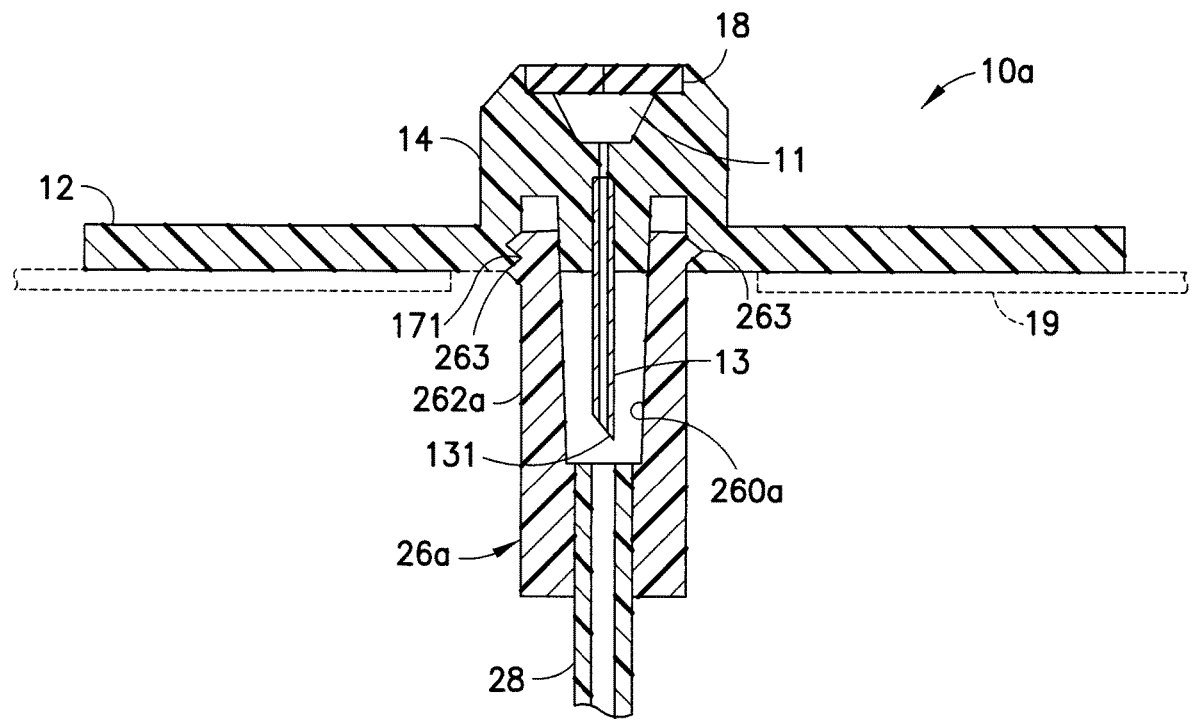
FIG. 8 is a cross-sectional view of the base of FIG. 7, illustrated with the connector attached to the base.

FIGS. 6-8 illustrate one embodiment of an infusion set in accordance with the present invention. In this embodiment, the infusion set 1a includes a line set 20 that is attachable to a base 10a. The line set 20 includes a hub 22 and a fluid tubing set 28 attached to the hub 22. An end of the fluid tubing set 28 is connected to a connector 26a, such as a conventional ISO 594 threaded connector sold under the trademark Luer-Lok®, that can attach to an infusate reservoir or pump (not shown). In accordance with the present invention, the base 10a includes an adapter 14 with a tapered or frusto-conical lower portion 16a whose diameter decreases in the direction from top to bottom, and a threaded cylindrical inner wall portion 17a. Space is formed between the lower portion 16a and the inner wall portion 17a, sufficient to receive the connector 26a. The connector 26a includes a tapered or frusto-conical inner wall 260a whose diameter decreases in the direction from top to bottom, and a cylindrical outer wall 262a. The tapers (nominally 6%) of the lower portion 16a and the frusto-conical inner wall 260a are matching or complementary. Threads 263 are formed on the outer wall 262a of the connector 26a (e.g., as in a Luer-Lok®) connector. The connector 26a is configured to attach to the base 10a. The threads 263 on the outer wall 262a of the connector 26a are configured to be rotatably attached onto corresponding threads or grooves 171 formed on the cylindrical inner wall portion 17a of the adapter 14, to detachably attach the connector 26a to the base 10a, as illustrated in FIG. 8.

The outer threads 263 also function as a Luer-Lok® connector to interface with corresponding grooves in the pump or reservoir (not shown) to administer the infusate to the user. FIG. 7 illustrates the base 10a with the hub 22 detached therefrom. The inner wall 17a of the adapter 14 includes threads or grooves 171 for receiving the threads 263 of the connector 26a.

FIG. 8 illustrates the base 10a with the connector 26a secured on the base 10a. The connector 26a is rotatably attached to be secured onto the base 10a. The threads 263 rotatably insert into the corresponding threads or grooves 171, to securely attach the connector onto the base 10a. Reversing the rotation of the connector 26a releases the connector 26a from the base 10a. The manner in which the hub 22 is secured onto the base 10a is similar to that illustrated in the embodiment of FIGS. 1-5. When the connector 23 is attached to the base 10a, as illustrated in FIG. 8, the cannula 13 is protected by the connector 23, with the part of the cannula 13 that extends from the lower portion 16a of the adapter 14 being housed in the space formed between the cylindrical inner wall 260a of the connector 26a, to prevent contact with the cannula 13, including its piercing tip 131.

Figure 9:
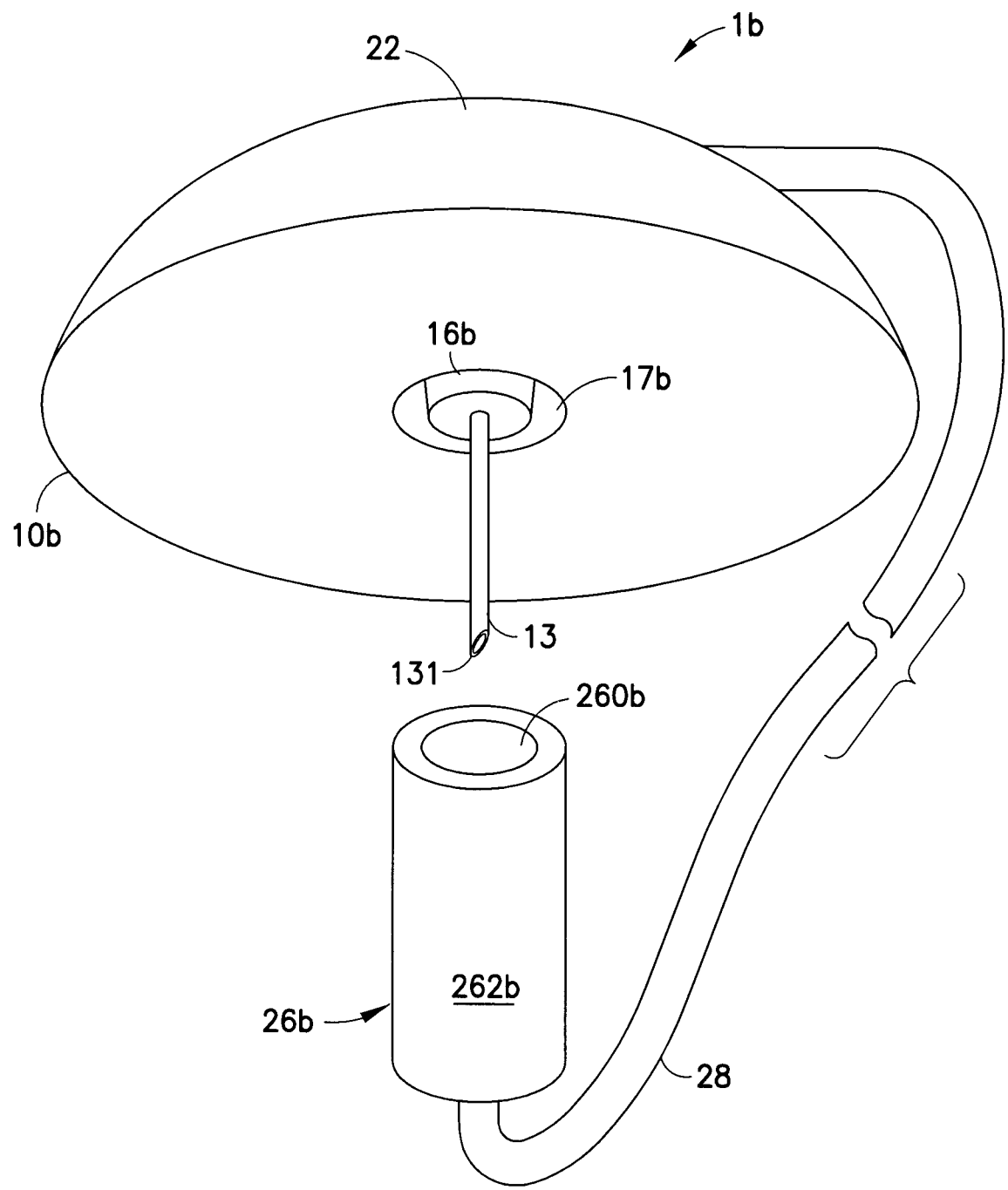
FIG. 9 is a perspective view of an exemplary infusion set of the present invention.
Figure 10:
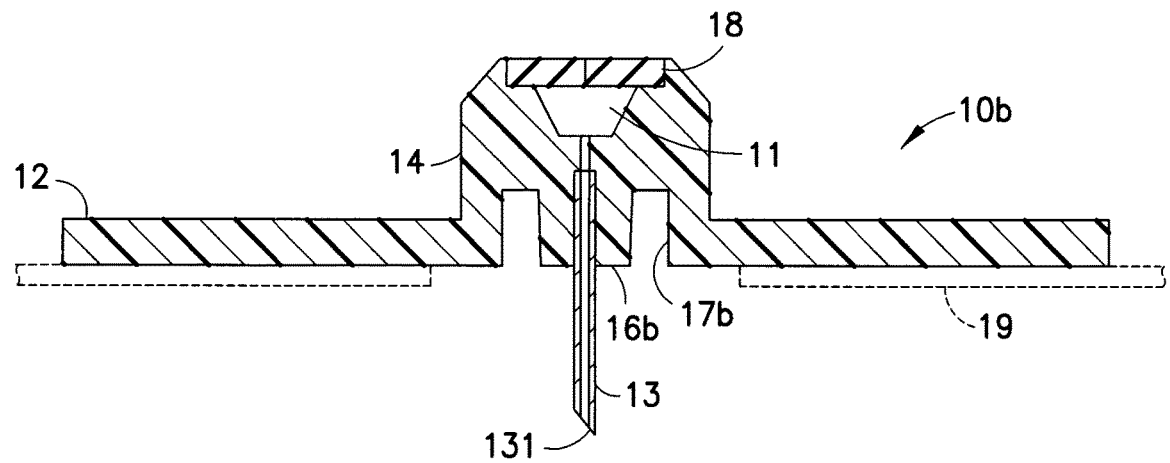
FIG. 10 is a cross-sectional view of the base of the infusion set of FIG. 9, after the hub has been removed from the base.
Figure 11:
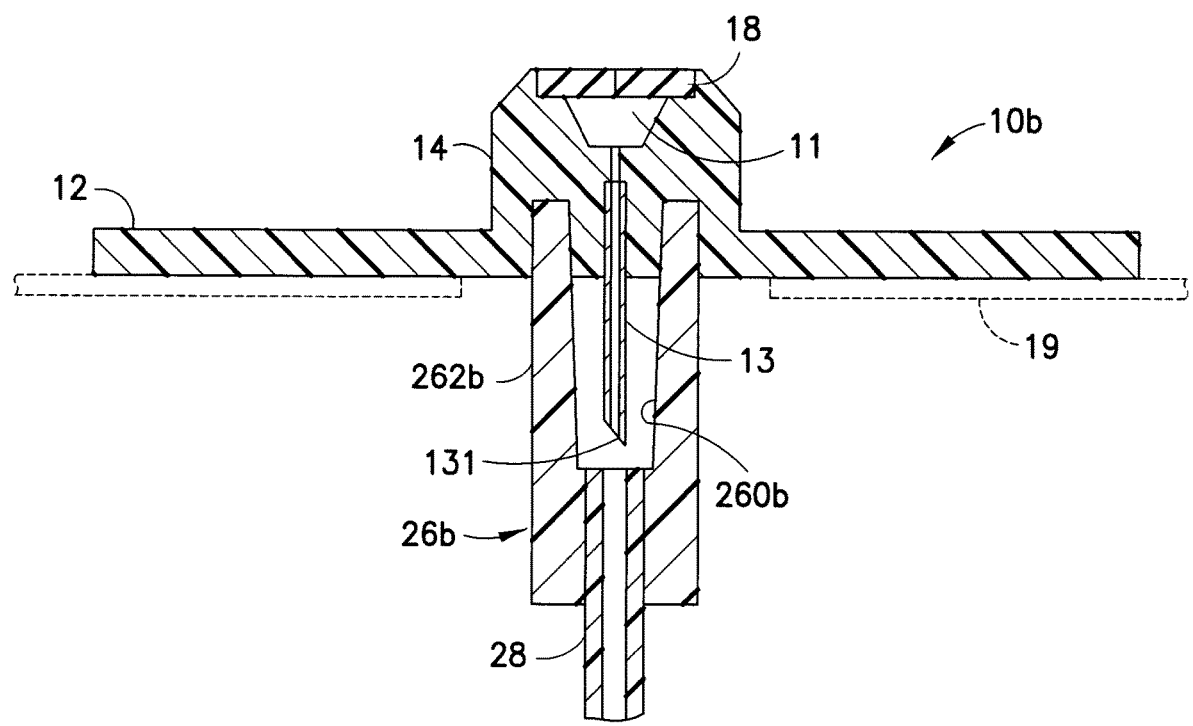
FIG. 11 is a cross-sectional view of the base of FIG. 10, illustrated with the connector attached to the base.

In a modification of the embodiment of FIGS. 6-8, as illustrated in FIGS. 9-11, in the infusion set 1b, the threads or grooves 171 and the threads 263 (of the embodiment of FIGS. 6-8) can be deleted and the attachment between the fluid connector 26b and the lower portion 16b of the base 10b can rely on the frictional interference between the mating tapered or frusto-conical surfaces of the lower portion 16b and inner wall 260b, similar to a conventional ISO 594 Luer-type slip fitting.

Figure 12:
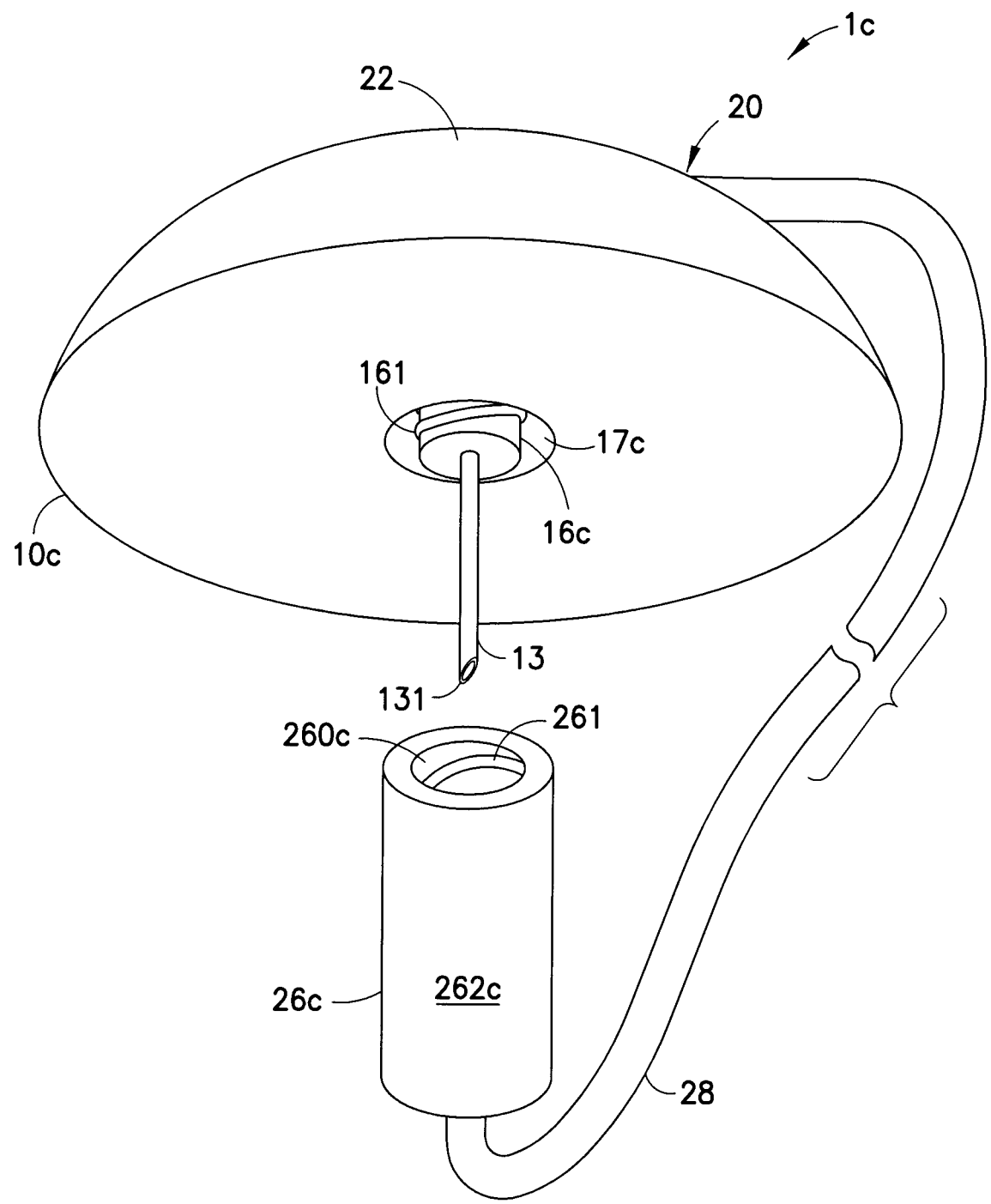
FIG. 12 is a perspective view of another exemplary steel cannula infusion set of the present invention.
Figure 13:
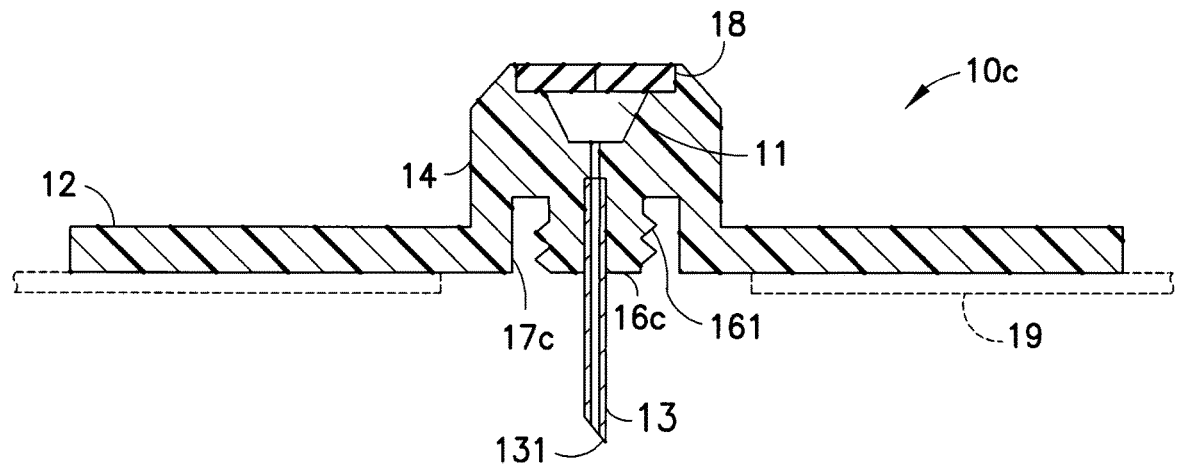
FIG. 13 is cross-sectional view of the base of the infusion set of FIG. 12, after the hub has been removed.
Figure 14:
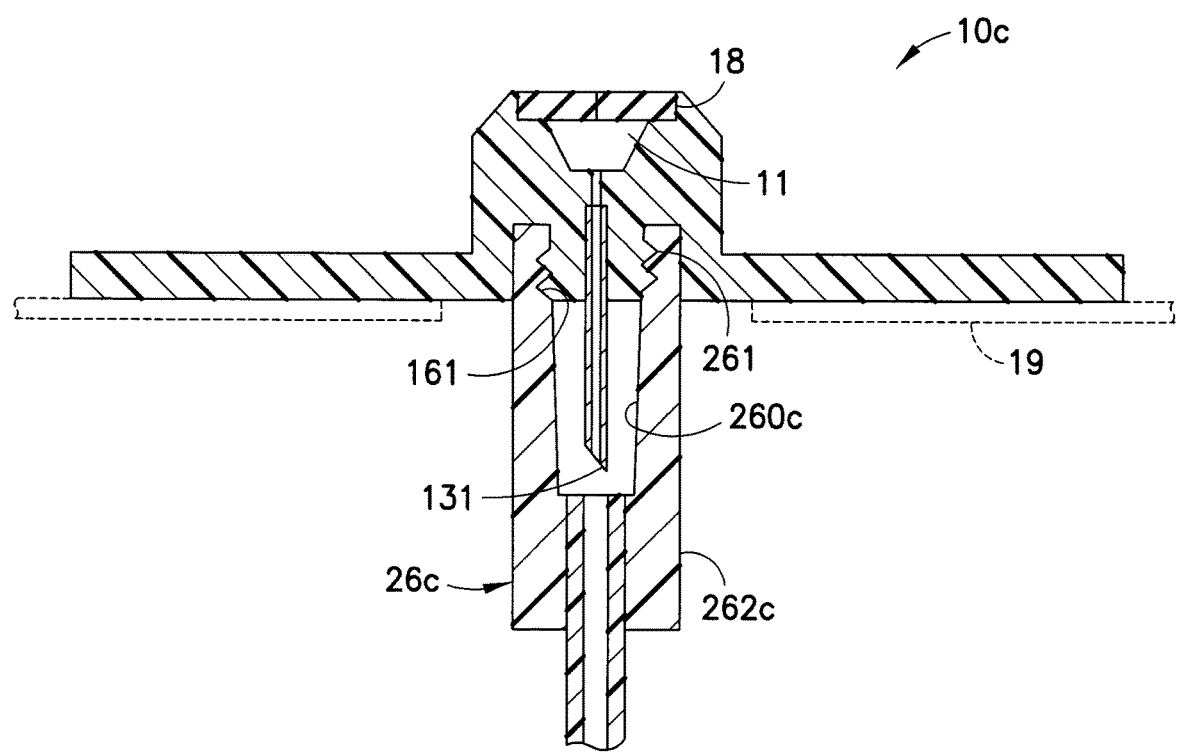
FIG. 14 is cross-sectional view of the base of FIG. 13, illustrated with the connector securely attached to the base.

FIGS. 12-14 illustrate another embodiment of an exemplary infusion set of the present invention. In this embodiment, an infusion set 1c includes a hub 22 attachable to a base 10c. In this embodiment, the lower portion 16c of the adapter 14 includes thread portions 161, and the inner wall 260c of the connector 26c includes corresponding threads or grooves 261 that receive the threads 161 when the connector 26c is rotatably attached to the base 10c. In this embodiment, which is not of the Luer type, the lower portion 16c and the inner wall 260c may be cylindrical rather than frusto-conical.

FIG. 13 is a cross-sectional view of the base 10c, illustrating the lower portion 16c of the adapter 14 having threads 161 on its outer surface. There is space between the inner wall portion 16c and the inner wall portion 17c of the adapter 14 to receive the connector 26c. In this space, the connector 26c can be secured to the base 10c. FIG. 14 illustrates the base, 10c with the connector 26c secured thereon. In this embodiment, the threads 161 of the lower portion 16c of the adapter are rotatably attached onto the corresponding grooves 261 of the inner wall of the connector 26c to attach the connector 26c to the base 10c. Thus, the steel cannula 13 is securely protected from unwanted external contact, in order to prevent unwanted or accidental contact with the tip 131 of the steel cannula 13 to avoid contamination.

Figure 15:
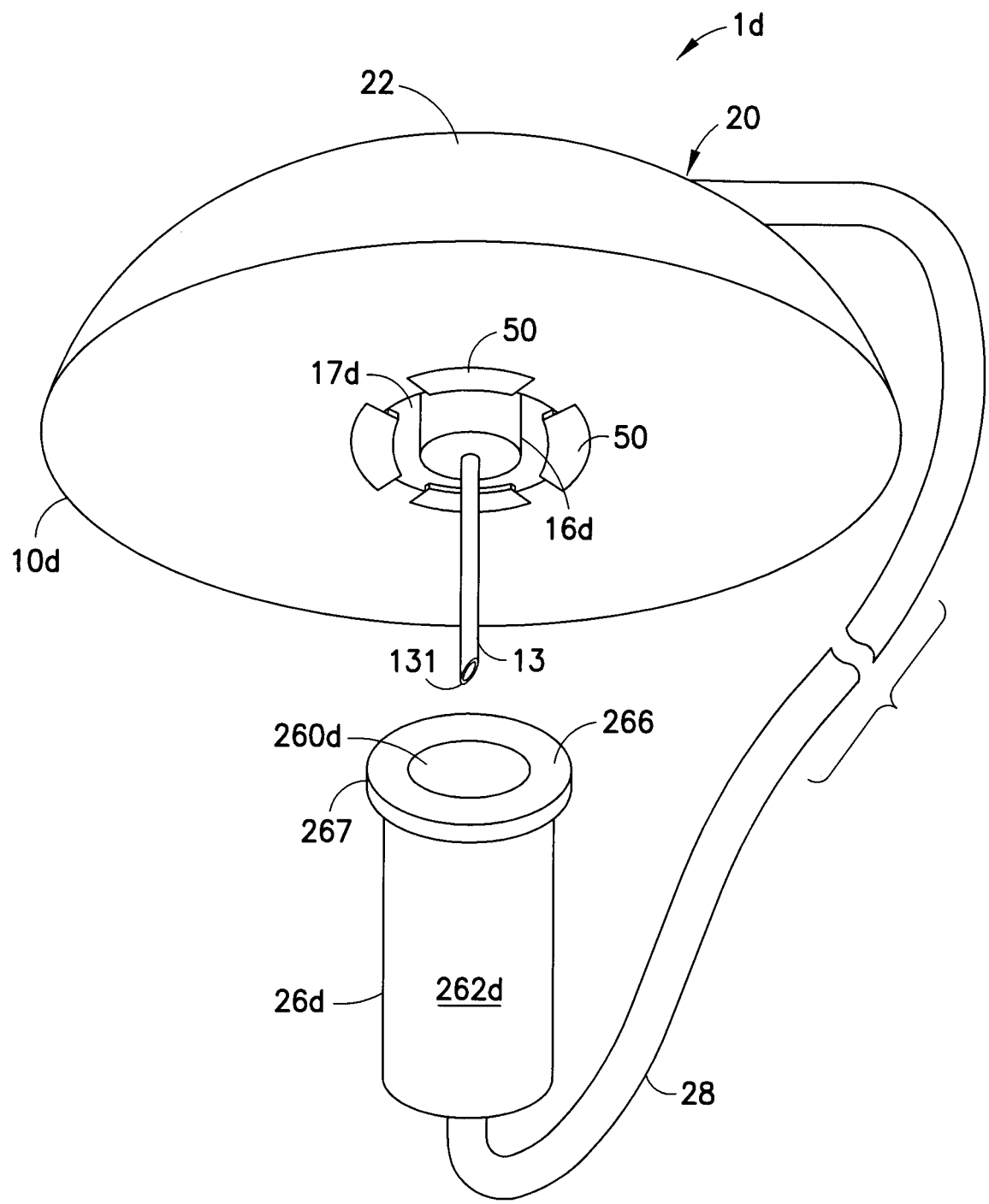
FIG. 15 is a perspective view of yet another exemplary steel cannula infusion set of the present invention.
Figure 16:
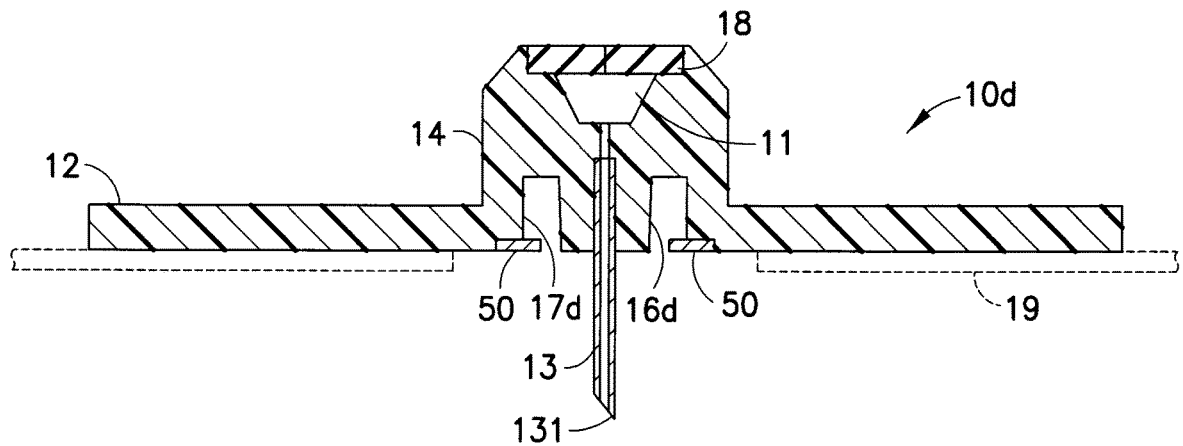
FIG. 16 is a cross-sectional view of the base of the infusion set of FIG. 15, after the hub has been detached from the base.
Figure 17:
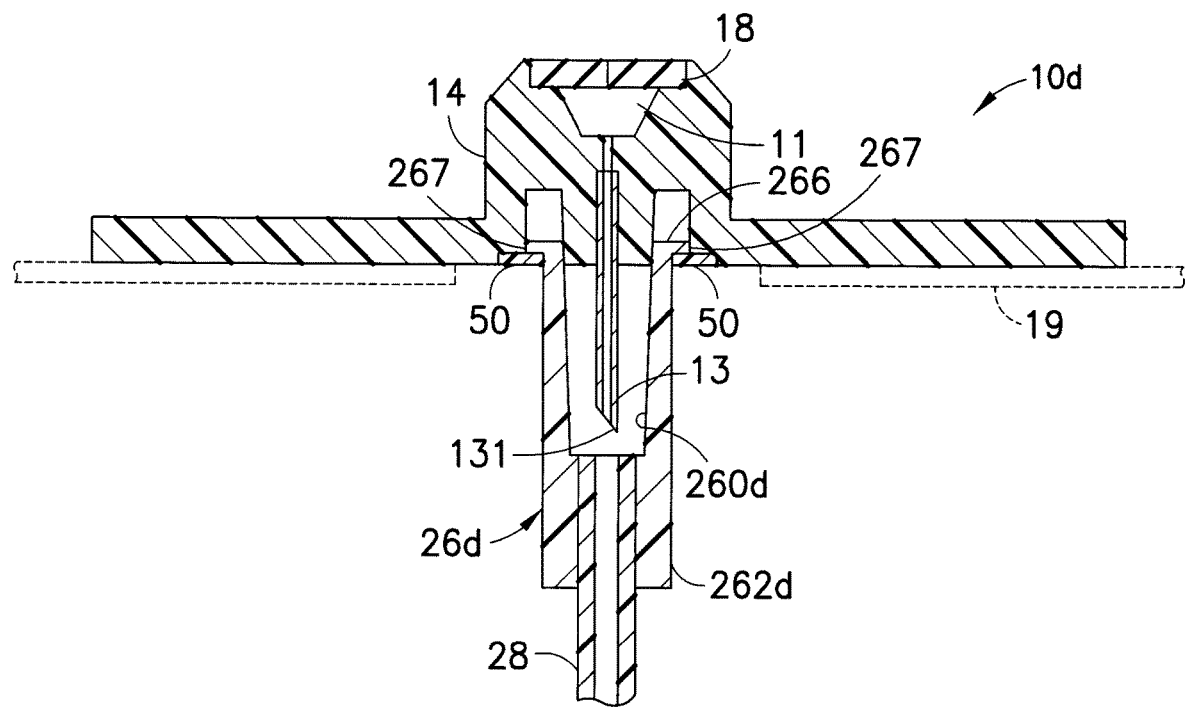
FIG. 17 is a cross-sectional view of the base of FIG. 16, illustrated with the connector attached to the base.

FIGS. 15-17 illustrate yet another embodiment of the infusion set of the present invention. In this embodiment, the infusion set 1d includes a base 10d onto which is attached a line set 20. The line set 20 includes a hub 22 and a fluid tubing set 28, with a connector 26d attached to an end portion thereof, as illustrated in FIG. 15. One or more flexible tabs 50 are attached to or formed integrally with a lower surface of the base 10d. The connector 26d includes an annular rib 266 and a cylindrical or frusto-conical inner wall 260d, such that the annular rib 266 can fit into the space between the inner wall portion 17d and the lower portion 16d of the adapter 14d, as the flexible tabs 50 deform to give way. When the flexible tabs 50 revert back to their original shapes, the flexible tabs 50 are able to retain the annular rib, as illustrated in FIG. 17, absent excessive pulling on the connector 26d. If the inner wall 260d is cylindrical, the lower portion 16d is also cylindrical. Similarly, if the inner wall 260d is frusto-conical, the lower portion 16d is also frusto-conical, to permit a Luer-type friction fit when the inner wall 260d engages the lower portion 16d, as illustrated in FIG. 17.

Figure 15A:
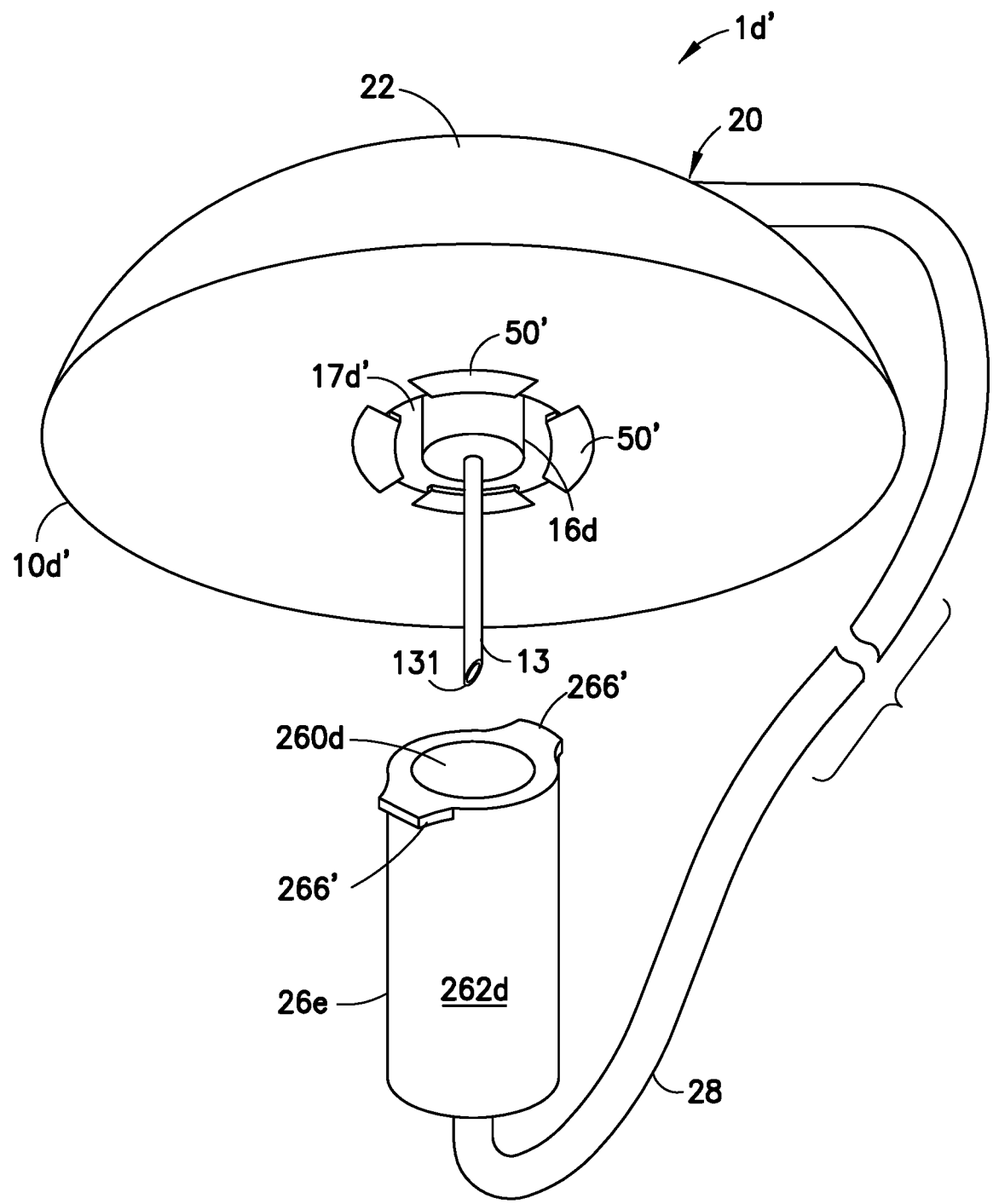
FIG. 15A illustrates a variation of the embodiment shown in FIG. 15.

FIG. 15A illustrates a variation of the embodiment of FIGS. 15. In this embodiment, the base 10d' includes one or more substantially rigid tabs 50' attached to or formed integrally with a lower surface of the base 10d'. The connector 26e of this embodiment includes one or more rigid tabs 266', such as Luer-Lok® thread segments, such that when the tabs 266' of the connector 26d are slotted into the spaces between the tabs 50' of the base 10d' and the connector 26d is rotated slightly, the tabs 266' and 50' can be frictionally engaged to bind the connector 26d to the base 10d', to provide a protective shield for the cannula 13.

FIG. 16 is a cross-sectional view of the infusion base 10d of FIG. 15, and illustrates the flexible tabs 50 secured on the bottom surface of the main base portion 12 of the base 10d. FIG. 17 illustrates the infusion base 10d with the connector 26d secured thereon, after the outer lip 267 of the annular rib 266 of the connector 26d has been inserted into the space between the inner wall portion 17d and the lower portion 16d of the adapter 14. The tabs 50 provide resistance to the outer lip 267 of the connector 26d to detachably secure the connector 26d to the adapter 10d, as illustrated in FIG. 17. It is conceivable that the one or more flexible tabs 50 can be formed on the lower portion 16d to secure the connector 26d to the base 10d.

In embodiments of the present invention, the protector 30 (illustrated in FIG. 5) in the form of a cylindrical tube that is typically included with infusion sets can be eliminated altogether. The connectors 26a, 26b, 26c, 26d and 26e in FIGS. 6-17 can render unnecessary such protectors 30 because the connectors 26a, 26b, 26c, 26d and 26e can be used to shield the steel cannula both before and after the infusion set is used, thereby eliminating a part that can be made redundant and reducing the overall cost of manufacture. The elimination of the plastic protectors 30 also eliminates the need to dispose of such protectors 30 that would otherwise have to be recycled or placed in landfills.

The infusion sets 1a, 1b, 1c, 1d and 1d' can be provided to users with respective connectors 26a, 26b, 26c, 26d and 26e that are attached to the bases 10a, 10b, 10c, 10d and 10d', such that in order to use the infusion sets, users first have to detach the respective connectors 26a, 26b, 26c, 26d and 26e from the bases 10a, 10b, 10c, 10d, 10d'to expose the cannulas 13 for attachment to the users for infusion therapy. After the bases 10a, 10b, 10c, 10d and 10d' with the cannulas 13 pierce the user's skin, infusion therapy can occur, as described above, with regard to FIGS. 1-5. Thereafter, after the user removes the base 10a, 10b, 10c, 10d, 10d' from the user's skin, and the connector 26a, 26b, 26c, 26d, 26e is detached from the pump or reservoir (not shown), the connector 26a, 26b, 26c, 26d, 26e can again be secured over the cannula 13 to protect the cannula 13, containing body fluids, from being contacted.

Thus, a component (protector 30) found in many infusion sets can be eliminated and the cannula 13 can be covered by a part (connector 26a, 26b, 26c, 26d) that is already a part of the infusion set 1a, 1b, 1c, 1d and 1d'. This solves the problem of proper disposal of used infusion sets that would otherwise be disposed of with cannulas that are exposed. In this manner, the cannulas of infusion sets can be protected before and after infusion therapy and used infusion sets can be securely transported or disposed, with the cannulas secured thereon.

Figure 1:
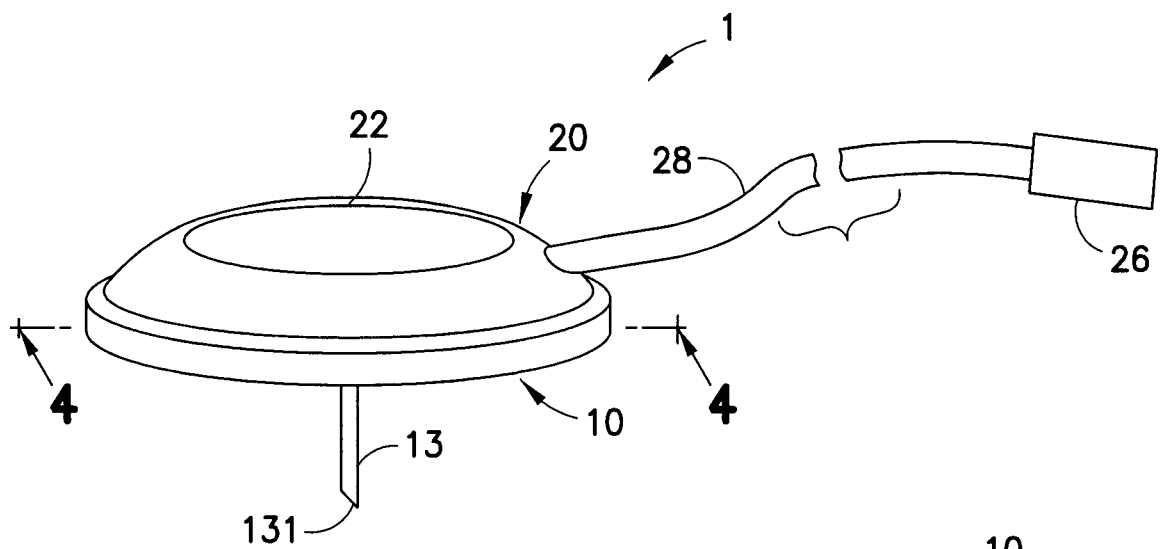
FIG. 1 is a perspective view of a steel cannula infusion set.
Figure 2:
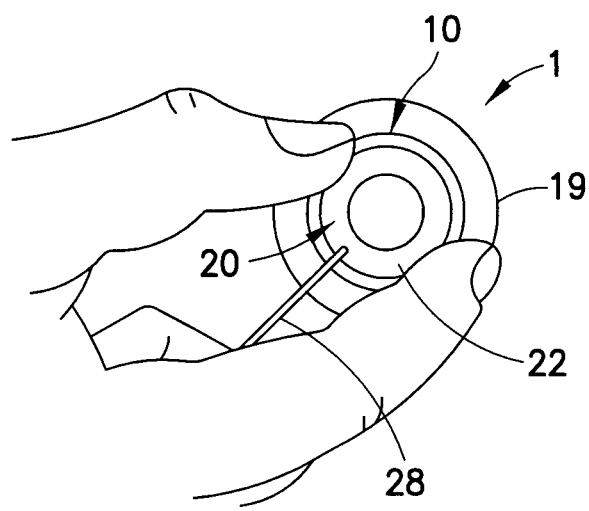
FIG. 2 is a top view of the infusion set of FIG. 1.
Figure 3:
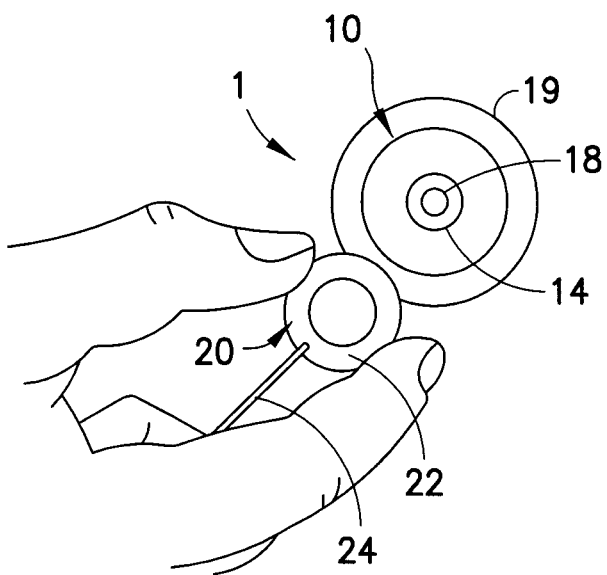
FIG. 3 is a top view of the infusion set of FIG. 1 in which the line set is detached from the base.
Figure 4:
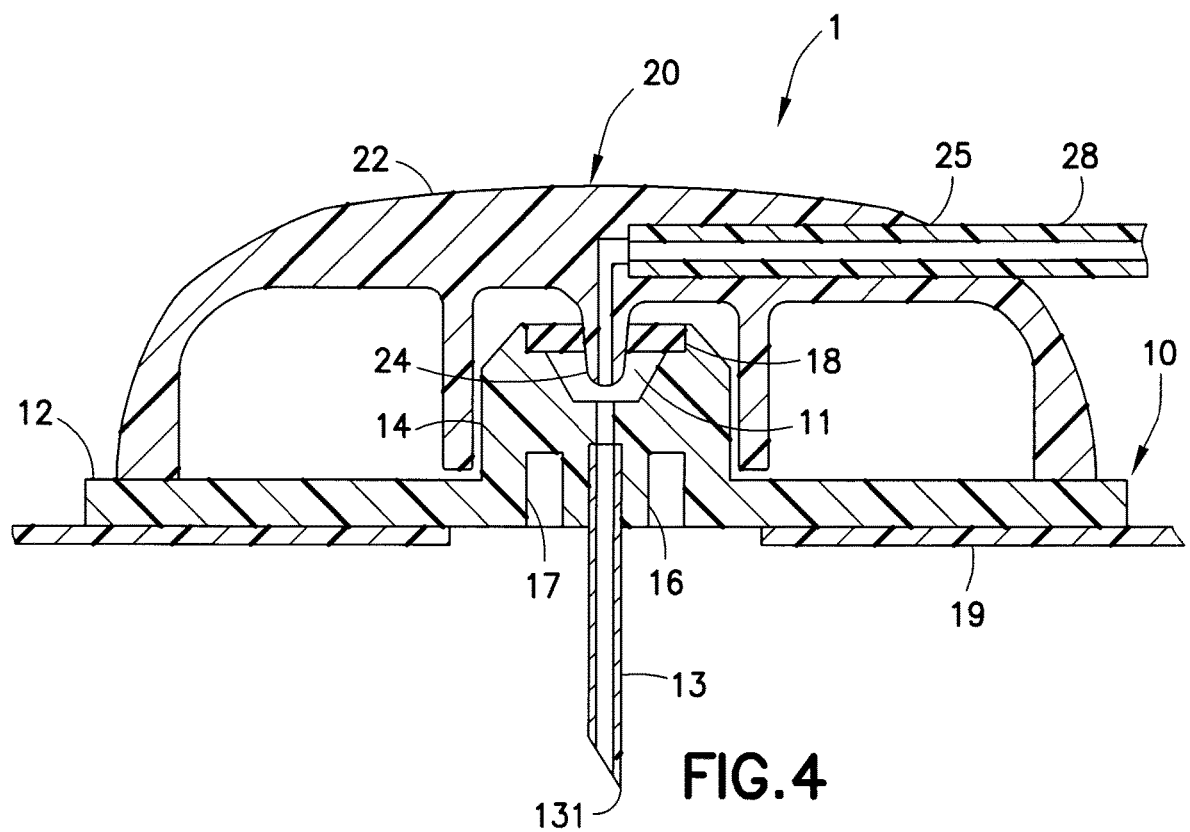
FIG. 4 is a cross-sectional view taken along lines 4-4 of the infusion set of FIG. 1.
Figure 5:
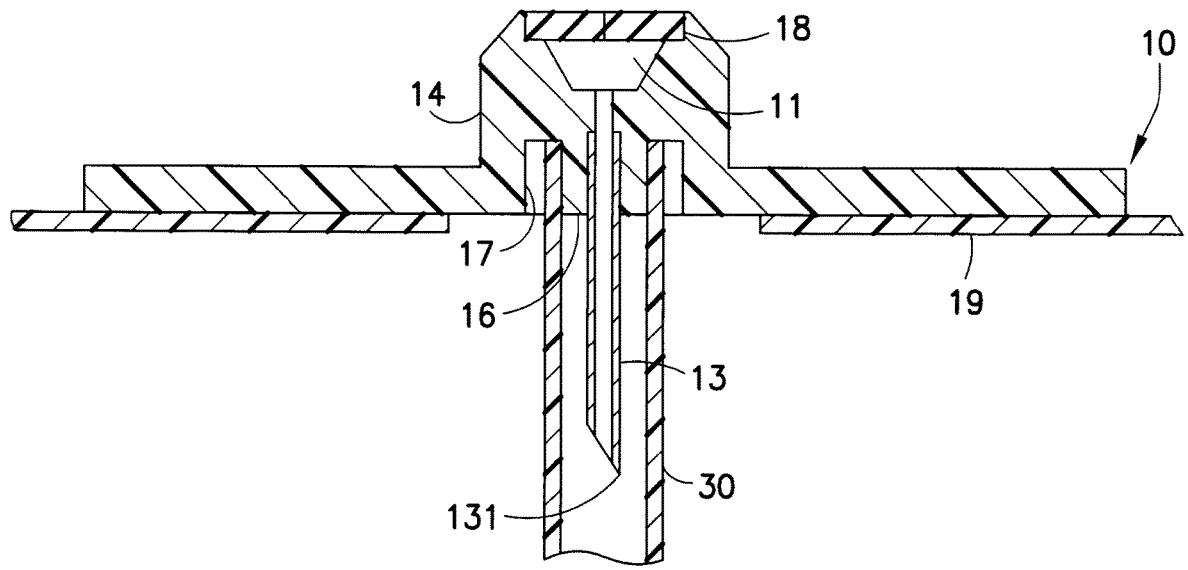
FIG. 5 is a cross-sectional view of the infusion set of FIG. 4, after the hub has been removed from the base.
Figure 18:
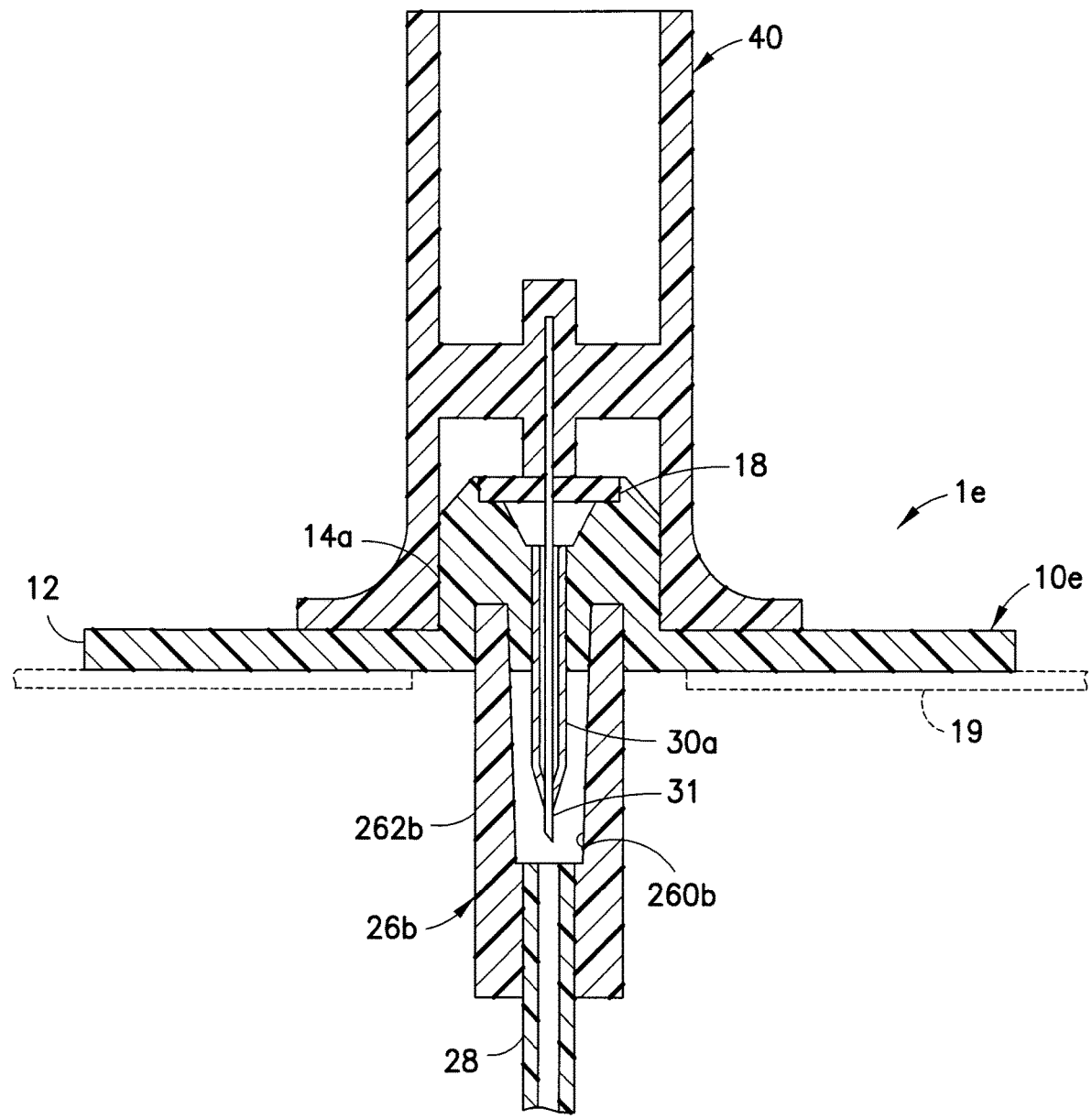
FIG. 18 is a cross-sectional view of another exemplary embodiment of the present invention directed to a soft catheter infusion set.

The embodiments described above relate to infusion sets that each include a cannula 13, one that is rigid and typically made of stainless steel. However, the present invention is not restricted to such types of infusion sets. FIG. 18 illustrates a base 10e of an infusion set 1e that utilizes a soft (e.g., Teflon®) catheter 30a instead of a rigid cannula to deliver infusate to a user. As is known in the art, in a soft catheter infusion set, in order to attach the soft catheter 30a into the skin of a user, an introducer needle 31 is inserted through the soft catheter 30a, as illustrated in FIG. 18, and the user pushes the needle hub 40 to which is attached the introducer needle 31 toward the user's skin so that the needle 31 and the soft catheter 30a both pierce the user's skin. Thereafter, the needle hub 40 is removed from the base 10e to remove the needle 31 from the user's skin while the soft catheter 30a remains in the user's skin. In accordance with the present invention, the infusion set can be configured such that the needle 31 and catheter 30a are both initially protected from exposure. Specifically, in the embodiment of FIG. 18, the needle hub 40 is initially placed on the base 10e, with the connector 26b attached to the base 10e protecting both the soft catheter 30a and the introducer needle 31. The manner of attachment of the connector 26b to the base 10e can be the same as that which is described for the cannula type infusion sets described in FIGS. 6-17. To permit infusion therapy, the needle 31 and needle hub 40 are removed and the line set hub 20 is placed on the base 10e, in the same manner as illustrated in FIG. 4.

Figure 19:
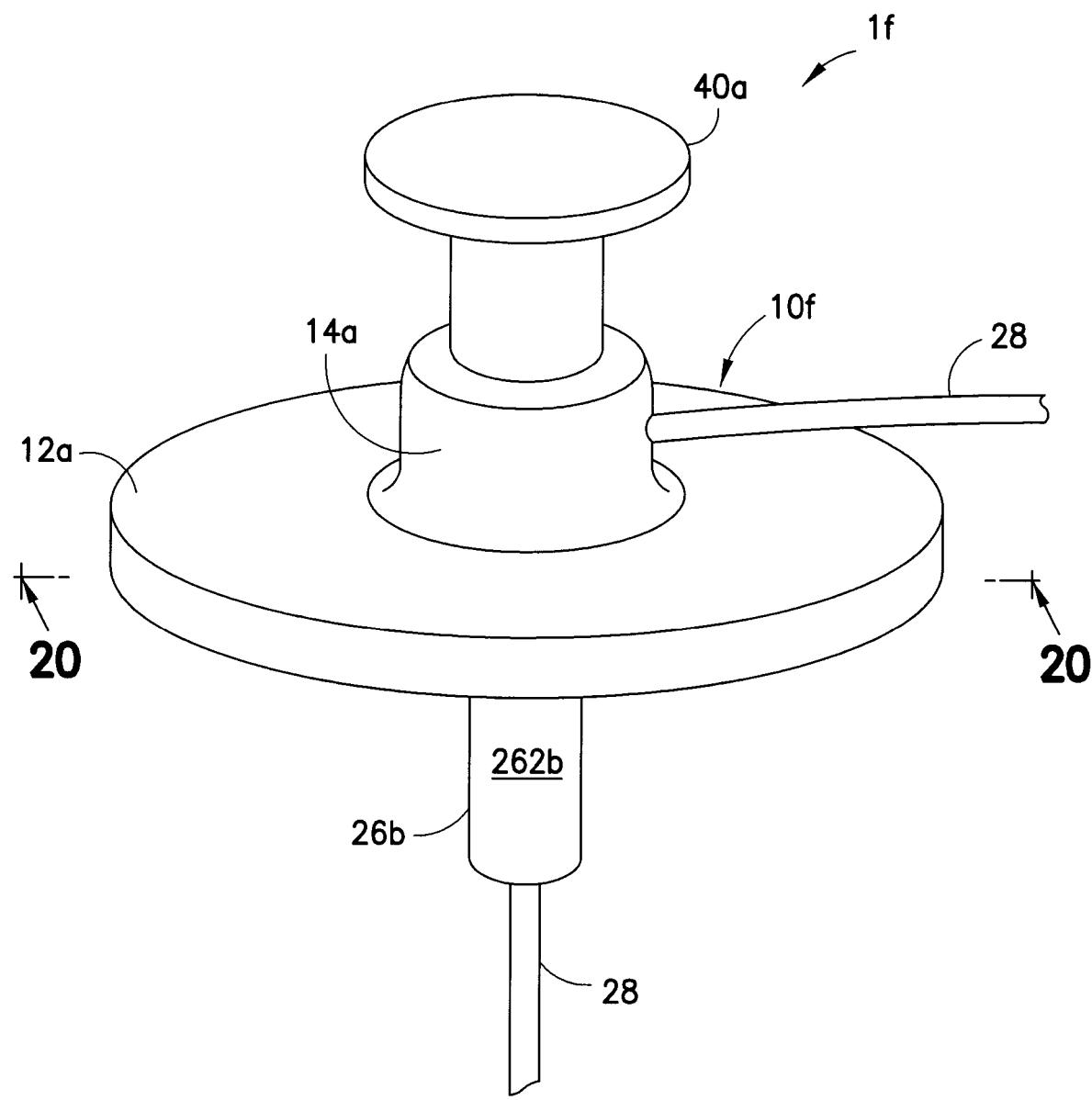
FIG. 19 is a perspective view of another exemplary infusion set.
Figure 20:
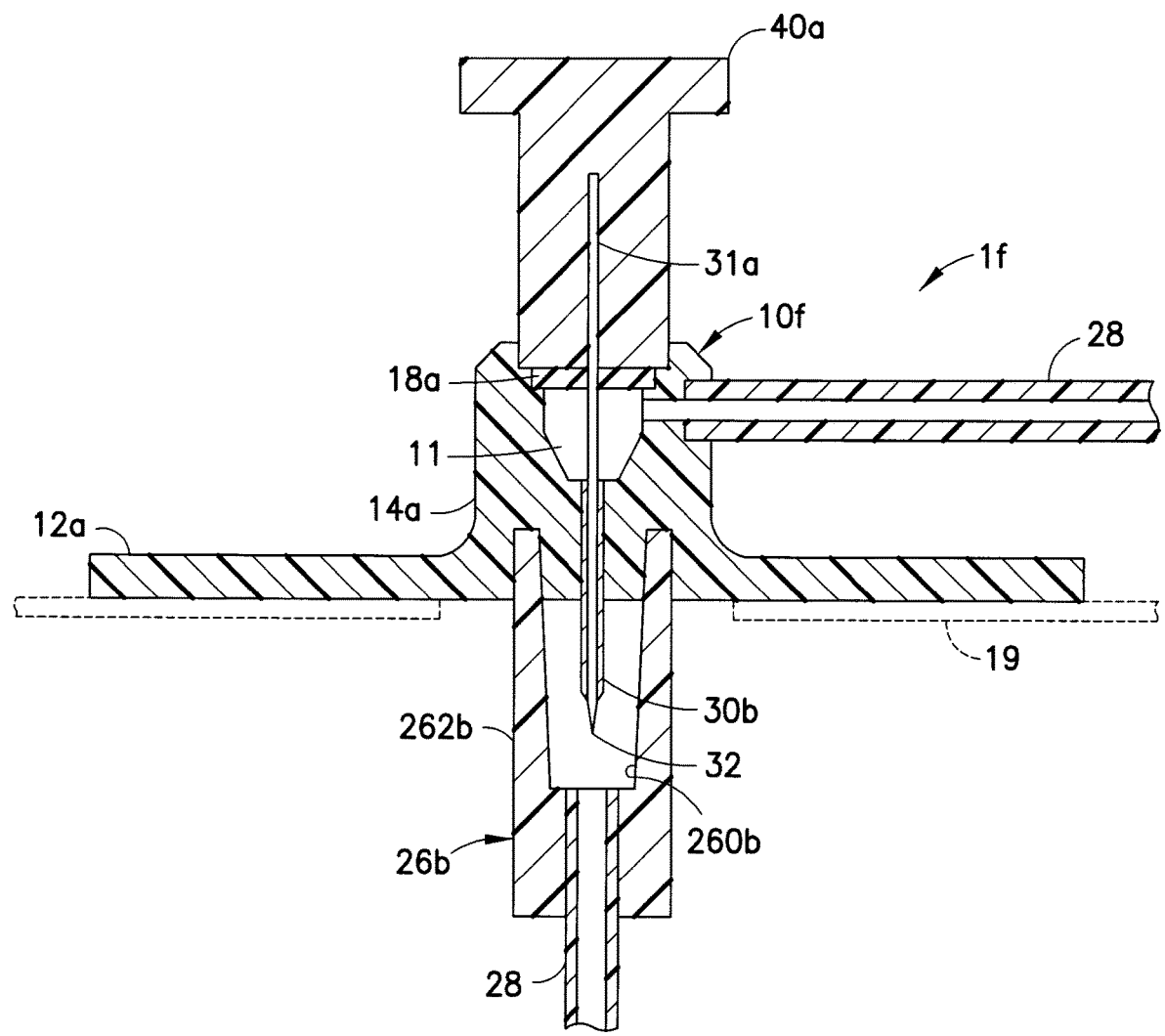
FIG. 20 is a cross-sectional view taken along lines 20-20 of the infusion set of FIG. 19.

FIGS. 19 and 20 illustrate another soft catheter infusion set 1f, in which the fluid tubing set 28 is permanently connected to the adapter 14a of the base 10f, such that when the needle hub 40a is removed after its needle 31a has penetrated, via its tip 32, the user's skin, infusion therapy can occur as infusate is dispensed from the tubing set 28, into the channel 11, and out through the catheter 30b. The self-sealing septum 18a self-closes after the needle 31a is removed from the catheter 30b and out through the septum 18a, as the needle hub 40a is removed from the infusion set 10a.

In the embodiment of FIGS. 19 and 20, the needle hub 40a can be placed on the base 10f, with the connector 26b attached to the adapter 14a, to protect both the soft catheter 30b and the introducer needle 31a. The manner of attachment of the connector 26b to the base 10f can be the same as that which is described for the cannula type infusion sets described in FIGS. 6-17.

Figure 21:
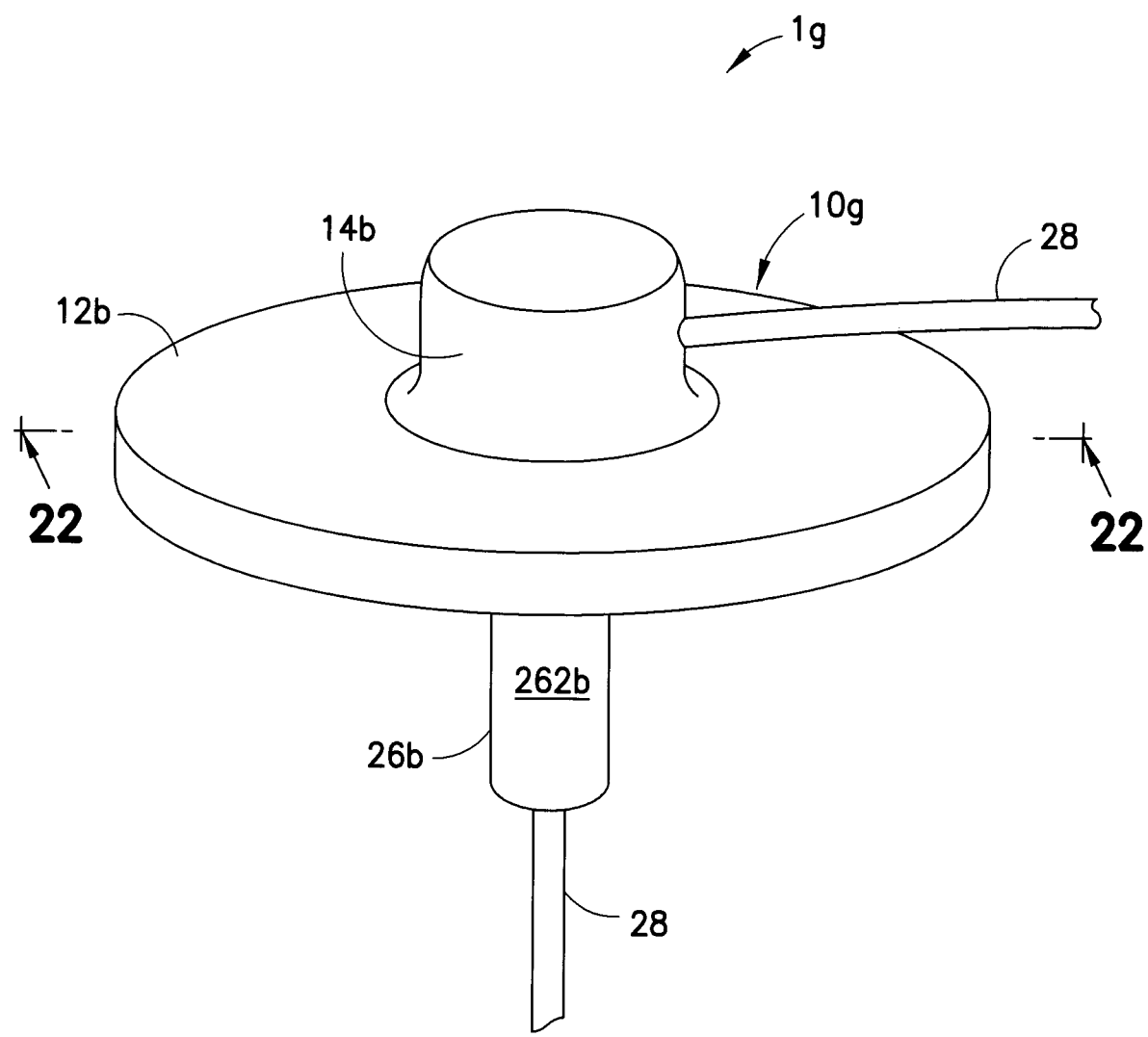
FIG. 21 is a perspective view of another exemplary infusion set.
Figure 22:
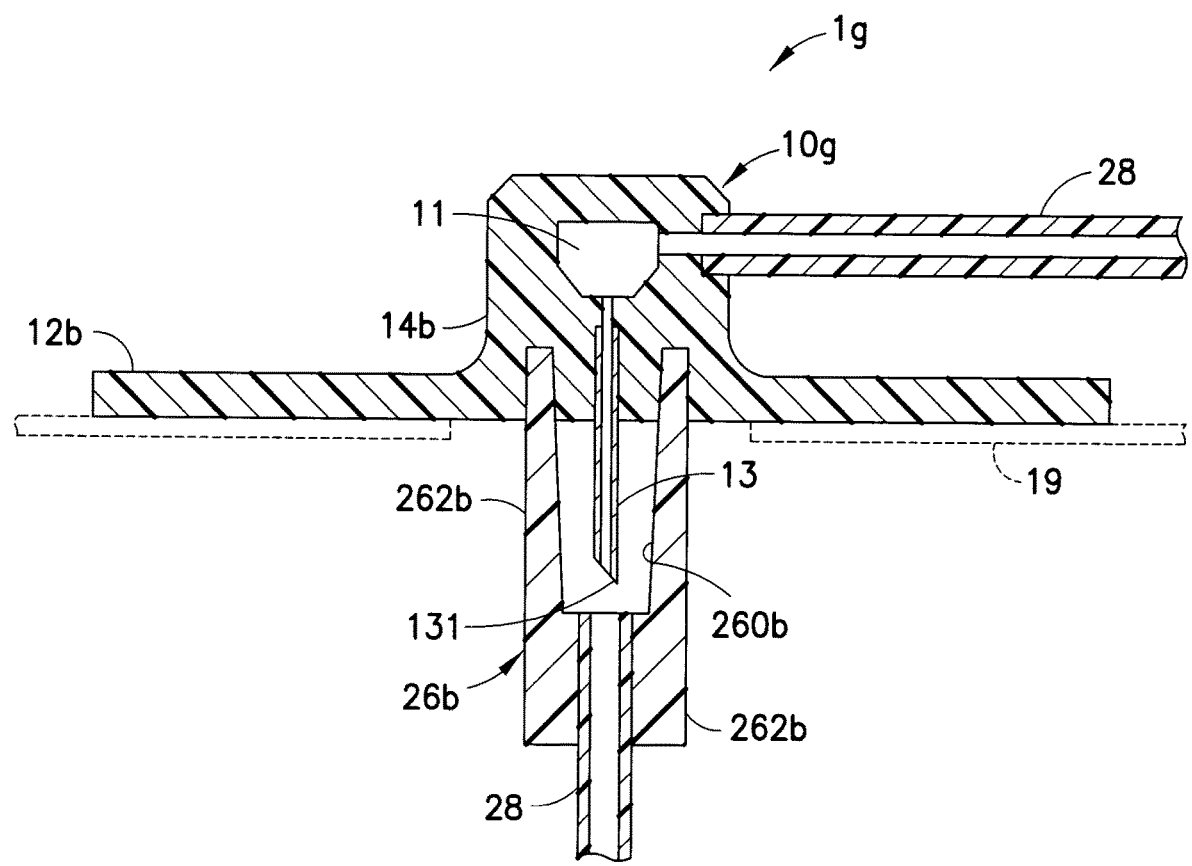
FIG. 22 is a cross-sectional view taken along lines 22-22 of the infusion set of FIG. 19.

The embodiment of FIGS. 21 and 22 is similar to that of the embodiment of FIGS. 19 and 20, except that this embodiment is directed to an infusion set 1g with a rigid or steel cannula 13 instead of a soft catheter. Since the rigid cannula 13 can penetrate the skin on its own, a separate introducer needle is not needed. The infusion set 1g includes a cannula 13 and a fluid tubing set 28 attached to the adapter 14b of the base 10g, such that the fluid tubing set 28, channel 11 and the cannula 13 are in fluid communication, to enable infusion therapy. Similar to the embodiments of FIGS. 6-17, in the embodiment of FIGS. 20 and 21, the manner of attachment of the connector 26b to the base 10g can be the same as that which is described for the cannula type infusion sets described in FIGS. 6-17.

Although only a limited number of embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the appended claims and their equivalents.

What is claimed is:

1. An infusion set comprising:
a connector including connector threads configured to attach to an infusion base when infusate is not being dispensed; and
the infusion base for attachment to a user of the infusion set, the infusion base comprising:
an adapter comprising adapter threads in one of a lower portion and an inner wall portion;
an infusion cannula extending from the adapter, the infusion cannula comprising a piercing part at an open end for piercing the user's skin; and
a gap between the lower portion and the inner wall portion, the adapter threads being configured to engage the connector threads for attachment to a pump, the connector being received in the gap.

2. An infusion set of claim 1, further comprising:
a line set comprising a fluid tubing set connected to a hub, the hub configured for attachment to the infusion base; and
the fluid tubing set comprising the connector for attachment to the pump; wherein
the pump is configured for pumping infusate from a reservoir to the hub via the fluid tubing set.

3. The infusion set as recited in claim 2, wherein an exterior surface of the connector includes the connector threads, the connector (1) being attached to the adapter threads to protect the piercing part of the infusion cannula when infusate is not being dispensed, and (2) being removable from the adapter threads and attachable to the pump for dispensing infusate.

4. The infusion set as recited in claim 2, wherein an interior surface of the connector is tapered.

5. The infusion set as recited in claim 1, wherein the inner wall portion includes the adapter threads.

6. The infusion set as recited in claim 1, wherein the lower portion is tapered and configured to complement an interior surface of the connector when engaged.

7. The infusion set as recited in claim 1, wherein
the adapter threads are configured to be attached to the connector threads to protect the piercing part of the infusion cannula when infusate is not being dispensed; and
the adapter threads are configured to be removable from the connector threads and the connector threads are configured to be attachable to the pump for dispensing infusate.

8. An infusion set comprising:
a base;
a needle or cannula attached to the base;
a fluid connector that is configured to attach to the base and a pump; and
means on the base for threadably detaching and attaching the fluid connector to the base so that the fluid connector covers the needle or cannula.

9. The infusion set of claim 8, wherein the means on the base for attaching the fluid connector to the base to cover the needle or cannula comprises at least one of a Luer taper, a Luer-Lok® connector, screw threads, and tabs.

10. The infusion set of claim 8, further comprising:
a line set comprising a fluid tubing set connected to a hub, the hub configured for attachment to the base; and
the fluid tubing set comprising the fluid connector for attachment to the pump; wherein
the pump is configured for pumping infusate from a reservoir to the hub via the fluid tubing set; and
the fluid connector is configured to attach to the base when infusate is not being dispensed.

11. The infusion set of claim 8, wherein
the base includes an adapter configured to be attached to the fluid connector to protect a piercing part of the needle or cannula when infusate is not being dispensed; and
the adapter is configured to be removed from the fluid connector and the fluid connector is configured to be attachable to the pump for dispensing infusate.

12. The infusion set of claim 8, further comprising
a tube set comprising one end attached to a hub and an open end, the open end of the tube set comprising the fluid connector, the fluid connector (1) being attached to the base to protect the piercing part of the infusion cannula when infusate is not being dispensed, and (2) being removable from the base and attachable to an infusion pump for dispensing infusate.

13. An infusion set comprising:
a base;
a catheter attached to the base;
a fluid connector that is configured to attach to the base and a pump; and
means on the base for threadably detaching and attaching the fluid connector to the base so that the fluid connector covers the catheter.

14. The infusion set of claim 13, wherein the means on the base for attaching the fluid connector to the base to cover the catheter comprises at least one of a Luer taper, a Luer-Lok® connector, screw threads, and tabs.

15. The infusion set of claim 13, further comprising:
a line set comprising a fluid tubing set connected to a hub, the hub configured for attachment to the base; and
the fluid tubing set comprising the fluid connector for attachment to the pump; wherein
the pump is configured for pumping infusate from a reservoir to the hub via the fluid tubing set; and
the fluid connector is configured to attach to the base when infusate is not being dispensed.

16. The infusion set of claim 13, wherein
the base includes an adapter configured to be attached to the fluid connector to protect a piercing part of the catheter when infusate is not being dispensed; and
the adapter is configured to be removed from the fluid connector and the fluid connector is configured to be attachable to the pump for dispensing infusate.

17. The infusion set of claim 13, further comprising
a tube set comprising one end attached to a hub and an open end, the open end of the tube set comprising the fluid connector, the fluid connector (1) being attached to the base to protect the piercing part of the infusion cannula when infusate is not being dispensed, and (2) being removable from the base and attachable to an infusion pump for dispensing infusate.

* * * * *